US010285570B2

(12) United States Patent
Ishizaki

(10) Patent No.: US 10,285,570 B2
(45) Date of Patent: May 14, 2019

(54) INSERTION INSTRUMENT AND INSERTION DEVICE

(71) Applicant: OLYMPUS CORPORATION, Tokyo (JP)

(72) Inventor: Ryosuke Ishizaki, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/620,890

(22) Filed: Jun. 13, 2017

(65) Prior Publication Data

US 2017/0273546 A1 Sep. 28, 2017

Related U.S. Application Data

(63) Continuation of application No. PCT/JP2016/060194, filed on Mar. 29, 2016.

(30) Foreign Application Priority Data

Jul. 2, 2015 (JP) .................................. 2015-133565

(51) Int. Cl.
*A61B 1/00* (2006.01)
*A61B 1/005* (2006.01)
*A61B 1/008* (2006.01)
*G02B 23/24* (2006.01)

(52) U.S. Cl.
CPC .......... *A61B 1/00133* (2013.01); *A61B 1/008* (2013.01); *A61B 1/0011* (2013.01);
(Continued)

(58) Field of Classification Search
CPC ............ A61B 1/00073; A61B 1/00135; A61B 1/00154; A61B 1/00156; A61B 1/0016;
(Continued)

(56) References Cited

U.S. PATENT DOCUMENTS

2014/0330079 A1* 11/2014 Ishizaki ............. A61B 1/00071
600/114

FOREIGN PATENT DOCUMENTS

JP 2015-144782 A 8/2015
WO WO 2013/038720 A1 3/2013
(Continued)

OTHER PUBLICATIONS

International Search Report dated Jun. 28, 2016 issued in PCT/JP2016/060194.
(Continued)

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

An insertion instrument includes a rotating member rotatable around a rotation axis, and adjacent portions adjacently provided on both sides of the rotating member in the direction along the rotation axis. The insertion instrument includes a cover tube forming a part of an outer surface of an insertion section and provided in an elastic deformation state so as to apply elastic force toward an inner peripheral side of the insertion section. A position of the rotating member in the direction along the rotation axis is adjusted by the elastic force, whereby a state where both ends of the rotating member in the direction along the rotation axis are located apart from the adjacent portions is maintained.

11 Claims, 10 Drawing Sheets

(52) U.S. Cl.
CPC .......... *A61B 1/0016* (2013.01); *A61B 1/0055* (2013.01); *A61B 1/00135* (2013.01); *A61B 1/00137* (2013.01); *A61B 1/00149* (2013.01); *G02B 23/24* (2013.01); *A61B 1/00073* (2013.01)

(58) Field of Classification Search
CPC ............ A61B 1/00131; A61B 1/00133; A61B 1/00137; E03F 9/005; H01R 39/28; H01R 39/64; B08B 9/045; B08B 9/047; F16H 7/02; F16H 57/01
See application file for complete search history.

(56) References Cited

FOREIGN PATENT DOCUMENTS

| WO | WO 2013/147017 A1 | 10/2013 |
| WO | WO 2014/208332 A1 | 12/2014 |
| WO | WO 2015/072233 A1 | 5/2015 |

OTHER PUBLICATIONS

English translation of International Preliminary Report on Patentability dated Jan. 11, 2018 together with the Written Opinion received in related International Application No. PCT/JP2016/060194.
Extended Supplementary European Search Report dated Aug. 9, 2018 in European Patent Application No. 16 81 7525.5.

\* cited by examiner

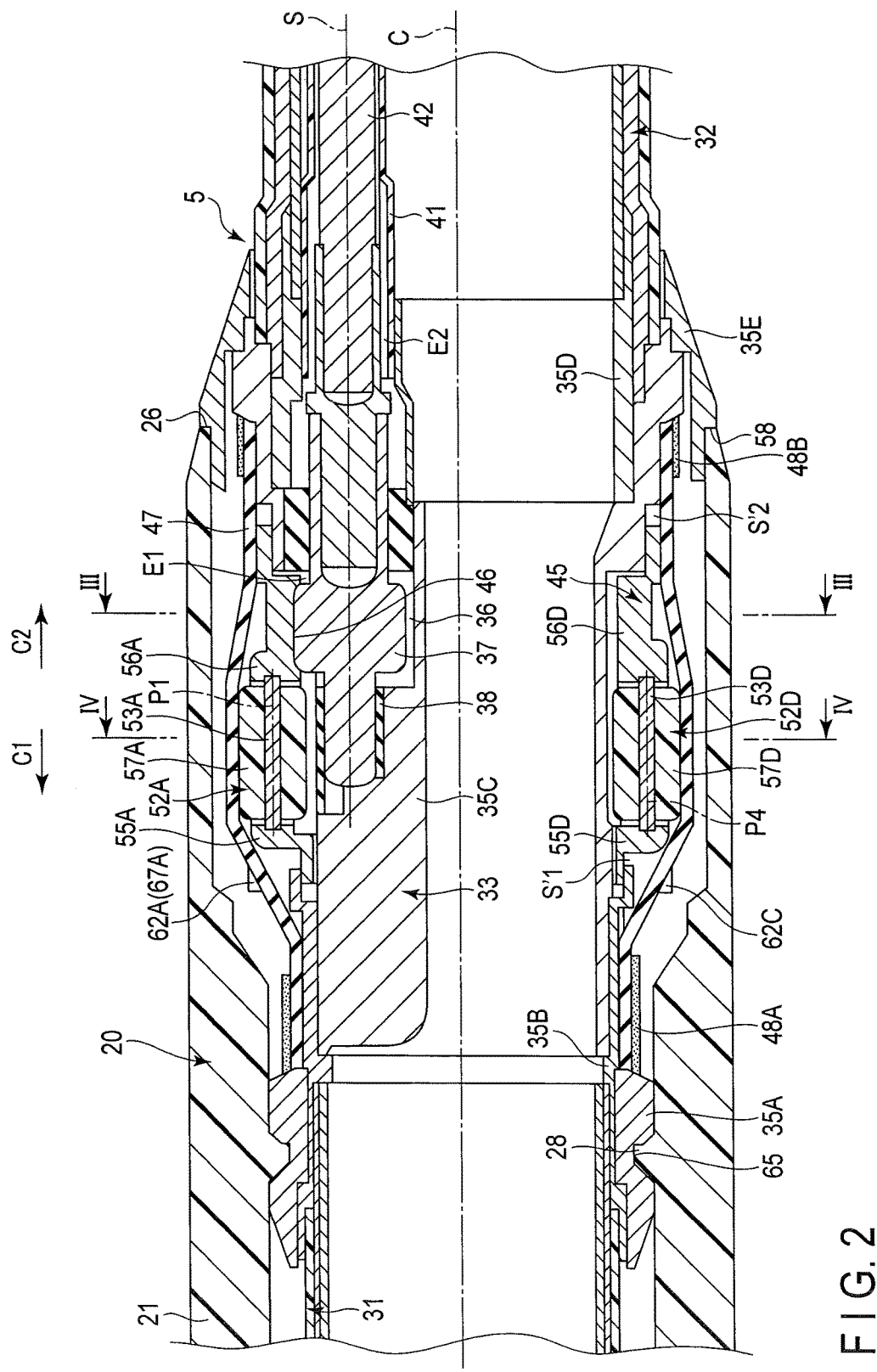
F I G. 2

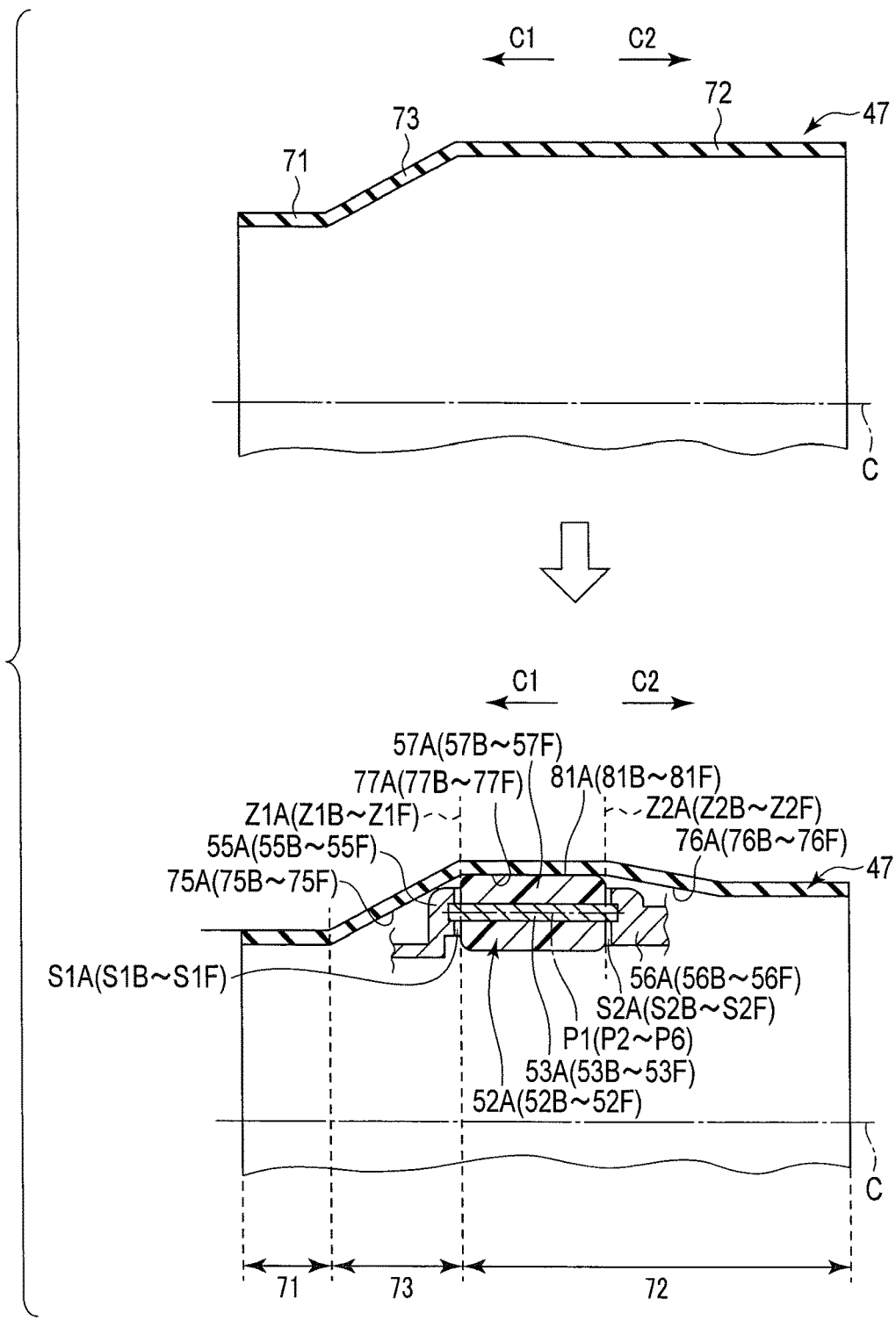
F I G. 6

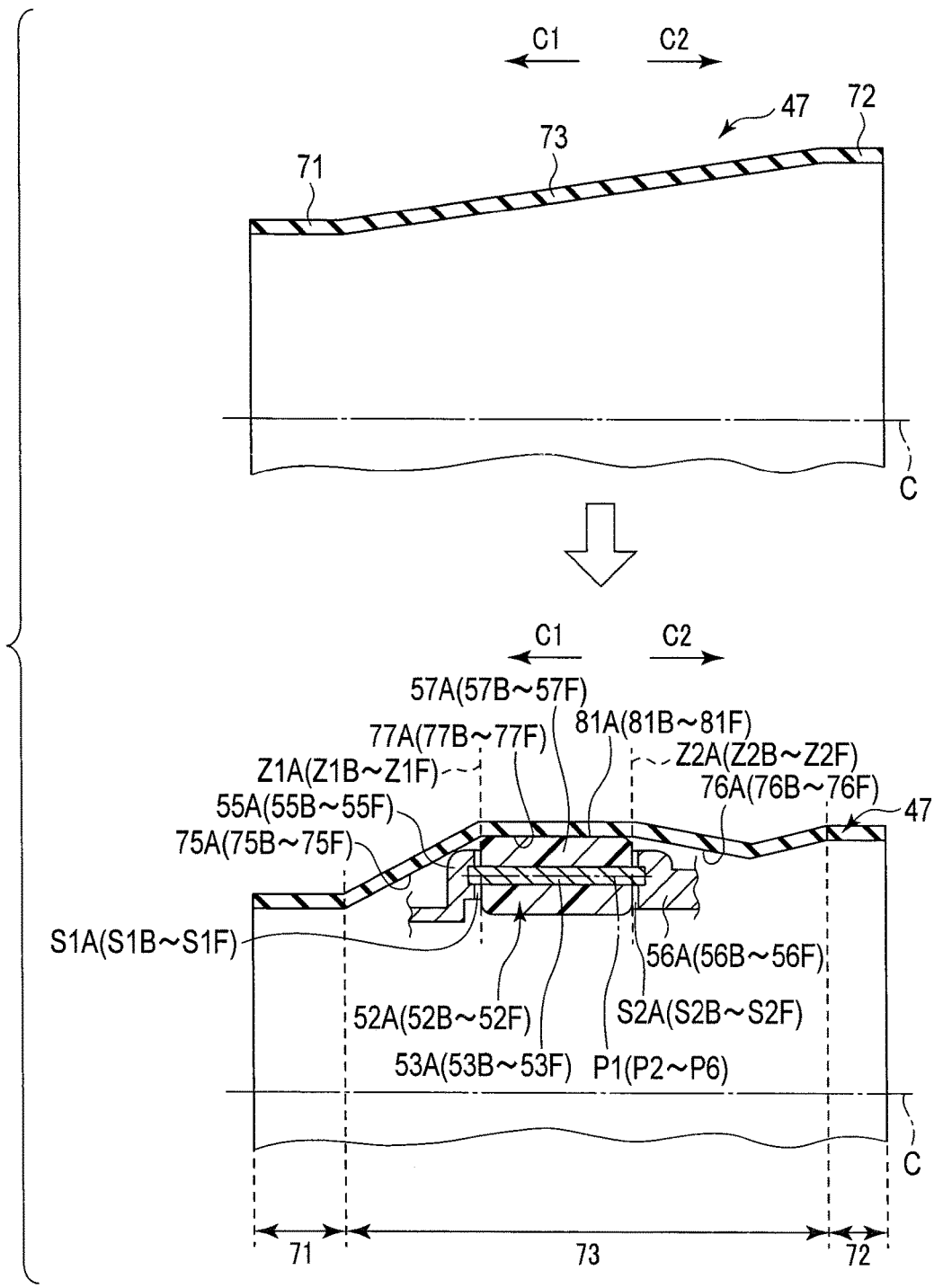
F I G. 9

INSERTION INSTRUMENT AND INSERTION DEVICE

CROSS-REFERENCE TO RELATED APPLICATIONS

This is a Continuation application of PCT Application No. PCT/JP2016/060194, filed Mar. 29, 2016 and based upon and claiming the benefit of priority from prior Japanese Patent Application No. 2015-133565, filed Jul. 2, 2015, the entire contents of which are incorporated herein by reference.

BACKGROUND OF THE INVENTION

1. Field of the Invention

The present invention relates to an insertion instrument in which a rotating member rotatable around a rotation axis is provided in an insertion section. Additionally, the present invention relates to an insertion device including the insertion instrument, and an assistance tool attached to the insertion section of the insertion instrument.

2. Description of the Related Art

International Publication No. 2013/038720 discloses a spiral unit (assistance tool) which is attached to an insertion section of an endoscope (insertion instrument). The spiral unit is detachably attached to the insertion section in a state of covering the insertion section from the outer peripheral side, and includes a spiral fin spirally extending around a longitudinal axis. In the insertion section, a rotating tubular member is attached to a base portion in a rotatable state around the longitudinal axis. Furthermore, to the rotating tubular member, rollers (rotating members) are attached, and each of the rollers is rotatable (turnable) relative to the rotating tubular member around a turning axis (roller axis) as a rotation axis (center). In the insertion section, a protrusion (first projection) which protrudes toward the outer peripheral side of the insertion section is formed owing to the presence of the roller (first roller), and in the spiral unit, there are provided projections (second projections) which protrude toward the inner peripheral side. The rollers and the rotating tubular member are covered, from the outer peripheral side, with a cover tube forming a part of the outer peripheral surface of the insertion section.

In a state where the spiral unit is attached to the insertion section, the rotating tubular member and the rollers rotate together around the longitudinal axis by the transmission of driving force thereto, whereby press force around the longitudinal axis acts on the corresponding projection of the spiral unit from each of the protrusions of the insertion section via the cover tube. Consequently, the driving force is transmitted to the spiral unit, and the spiral unit rotates relative to the base portion around the longitudinal axis. In this instance, each of the rollers forming the corresponding projection turns around the roller axis. Thus, friction between the projection (roller) and the cover tube decreases.

BRIEF SUMMARY OF THE INVENTION

According to one aspect of the invention, an insertion instrument including: an insertion section extending from a proximal side to a distal side along a longitudinal axis; a rotating member which is provided in the insertion section, and which is rotatable around a rotation axis; adjacent portions which are adjacently provided on both sides of the rotating member in a direction along the rotation axis, and to which the rotating member is rotatably attached; and a cover tube which forms a part of an outer surface of the insertion section, and which is provided in an elastic deformation state so as to apply elastic force toward an inner peripheral side of the insertion section, the cover tube being configured to adjust a position of the rotating member in the direction along the rotation axis by the elastic force, and thereby configured to maintain a state where both ends of the rotating member are located apart from the adjacent portions in the direction along the rotation axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view schematically showing the configurations of the insertion section and the spiral unit in an attachment part in which a spiral unit is attached to an insertion section and in the vicinity of the attachment part, in a state where the spiral unit is attached to the insertion section, according to the first embodiment;

FIG. 6 is a schematic diagram illustrating a state where a cover tube is not elastically deformed, and a state where the cover tube is elastically deformed by pressure from each of first projections, according to the first embodiment;

FIG. 9 is a schematic diagram illustrating a state where the cover tube is not elastically deformed, and a state where the cover tube is elastically deformed by the pressure from each of the first projections, according to a third modification of the first embodiment;

DETAILED DESCRIPTION OF THE INVENTION

First Embodiment

Figure 1:
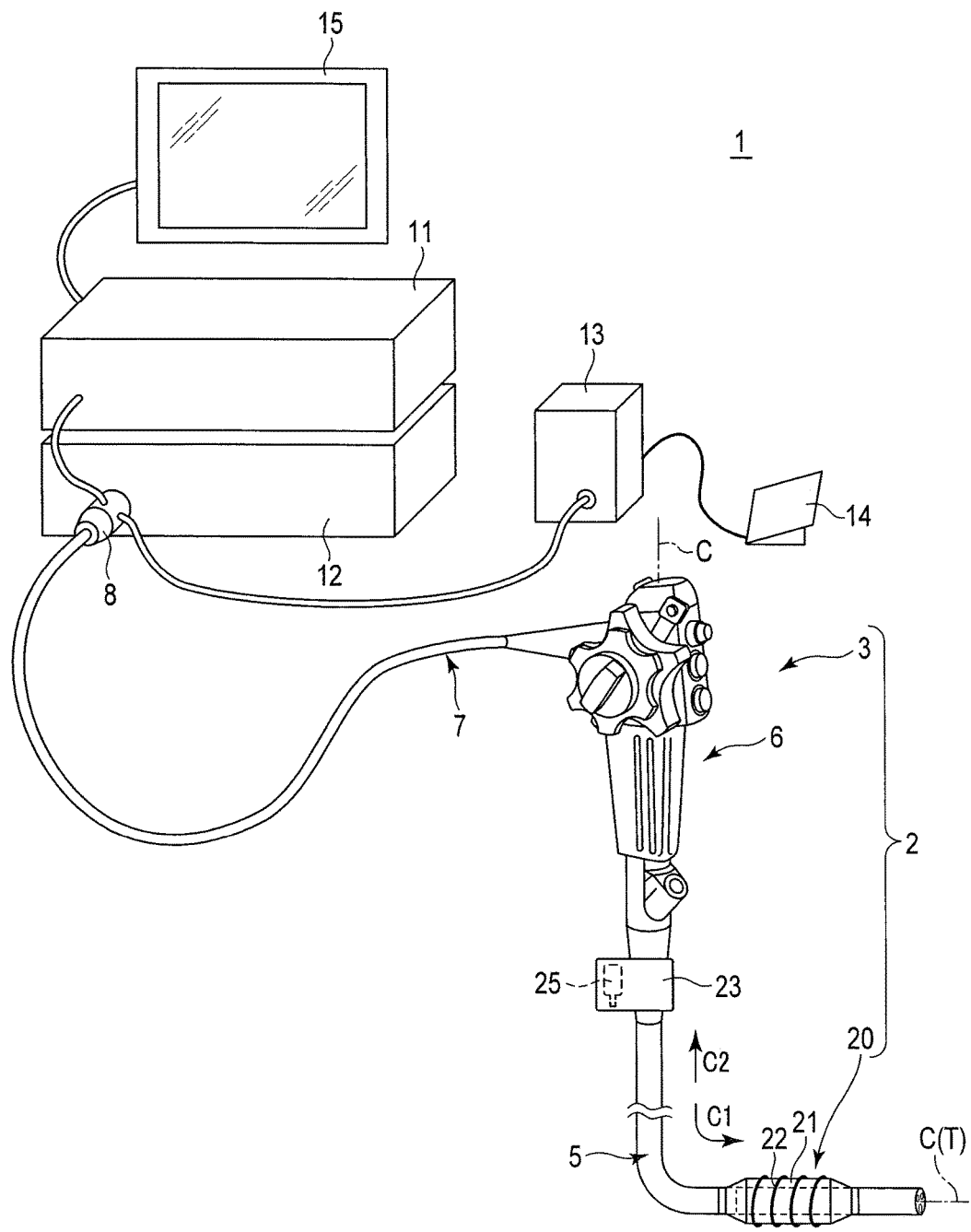
FIG. 1 is a perspective view schematically showing an endoscope system in which an endoscope device is used according to a first embodiment.

A first embodiment of the present invention is described with reference to FIG. 1 to FIG. 6. FIG. 1 is a diagram showing an endoscope system 1 in which an endoscope device 2 that is an insertion device is used. As shown in FIG. 1, the endoscope device 2 includes an endoscope 3 which is an insertion instrument, and a spiral unit 20 which is an assistance tool. The endoscope 3 includes an insertion section 5, and the insertion section 5 has a longitudinal axis C. Here, a direction along the longitudinal axis C is a longitudinal direction. One side in the longitudinal direction is a distal side (an arrow C1 side in FIG. 1), and the side opposite to the distal side is a proximal side (an arrow C2 side in FIG. 1). The insertion section 5 extends from the proximal side to the distal side along the longitudinal axis C, and an operation section 6 is provided on the proximal side of the insertion section 5 in the endoscope 3. The endoscope 3 includes a universal cord 7 having one end connected to the operation section 6. A scope connector 8 is provided at the other end of the universal cord 7.

As peripheral devices, the endoscope system 1 includes an image processing device 11 such as an image processor, a light source device 12 such as a lamp, a driving control device 13, an operation input device 14 such as a foot switch, and a display device 15 such as a monitor. The universal cord 7 is detachably connected to the light source device 12 via the scope connector 8. In the endoscope 3, an imaging cable (not shown) and a light guide (not shown) extends through an inside of the insertion section 5, an inside of the operation section 6, and an inside of the universal cord 7. An imaging element (not shown) such as a CCD is provided in the distal portion of the insertion section 5. The imaging element images a subject through an observation window (not shown) provided in the outer surface of the distal portion of the insertion section 5. An imaging signal is then transmitted to the image processing device 11 via the imaging cable, and image processing is performed in the image processing device 11. Thus, an image of the subject is generated in the image processing device 11, and the generated image of the subject is displayed on the display device 15. Light emitted from the light source device 12 is guided through the light guide. The guided light is then applied to the subject from an illumination window (not shown) provided on the outer surface of the distal portion of the insertion section 5.

In the endoscope device 2, the spiral unit (assistance tool) 20 is detachably attached to the insertion section 5 in a state where the insertion section 5 is inserted through the spiral unit 20. In a state where the spiral unit 20 is attached to the insertion section 5, the spiral unit 20 is substantially coaxial with the insertion section 5. The spiral unit 20 includes a cylindrical tube main body 21 extending along the longitudinal axis C, and a spiral fin 22 protruding toward the outer peripheral side on the outer peripheral surface of the tube main body 21. The spiral fin 22 spirally extends around the longitudinal axis C. The spiral unit (assistance tool) 20 is rotatable around the longitudinal axis C.

In the endoscope 3, a motor casing 23 is attached to the operation section 6. An electric motor 25 which is a driving member is provided inside the motor casing 23. One end of an electric wiring line (not shown) is connected to the electric motor 25. The electric wiring line is connected to the driving control device 13 with passing through the inside of the operation section 6 and the inside of the universal cord 7. The driving control device 13 controls the supply state of driving electric power to the electric motor 25 on the basis of an operation input in the operation input device 14, and controls the driving state of the electric motor 25. A processor or an integrated circuit including a central processing unit (CPU) or an application specific integrated circuit (ASIC) or the like, and a storage medium such as a memory are provided in the driving control device 13. The electric motor 25 is driven by the supply of the driving electric power to the electric motor 25, and thereby driving force to rotate (revolve) the spiral unit 20 around the longitudinal axis C is generated.

FIG. 2 is a diagram showing the configurations of the insertion section 5 and the spiral unit 20 in an attachment part in which the spiral unit 20 is attached to the insertion section 5 and in the vicinity of this part. FIG. 2 shows a state where the spiral unit 20 is attached to the insertion section 5. In FIG. 2, the imaging cable, the light guide, and others are omitted. As shown in FIG. 2, the insertion section 5 includes a distal side flexible tube section 31, and a proximal side flexible tube section 32 provided on the proximal side with respect to the distal side flexible tube section 31. The proximal end of the proximal side flexible tube section 32 is connected to the operation section 6. A base portion 33 made of a rigid material is provided between the distal side flexible tube section 31 and the proximal side flexible tube section 32. That is, the distal side flexible tube section 31 is coupled to the proximal side flexible tube section 32 via the base portion 33. In a state where the spiral unit 20 is attached to the insertion section 5, the outer peripheral side of the base portion 33 is covered with the proximal portion of the spiral unit 20, and the spiral unit 20 extends toward the distal side from a part located on the outer peripheral side of the base portion 33. Although the base portion 33 is formed by the coupling of five coupling members 35A to 35E in the present embodiment, the number of members that form the base portion 33 is not limited to this, and, for example, the base portion 33 may be integrally formed from one member.

Figure 3:
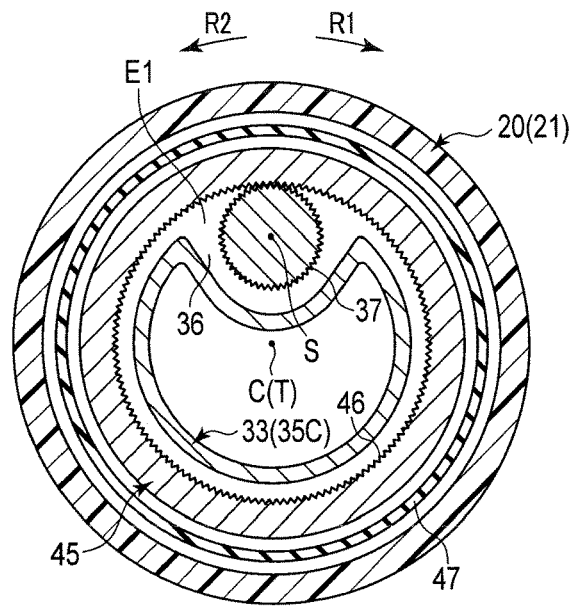
FIG. 3 is a sectional view taken along the line III-III in FIG. 2.
Figure 4:
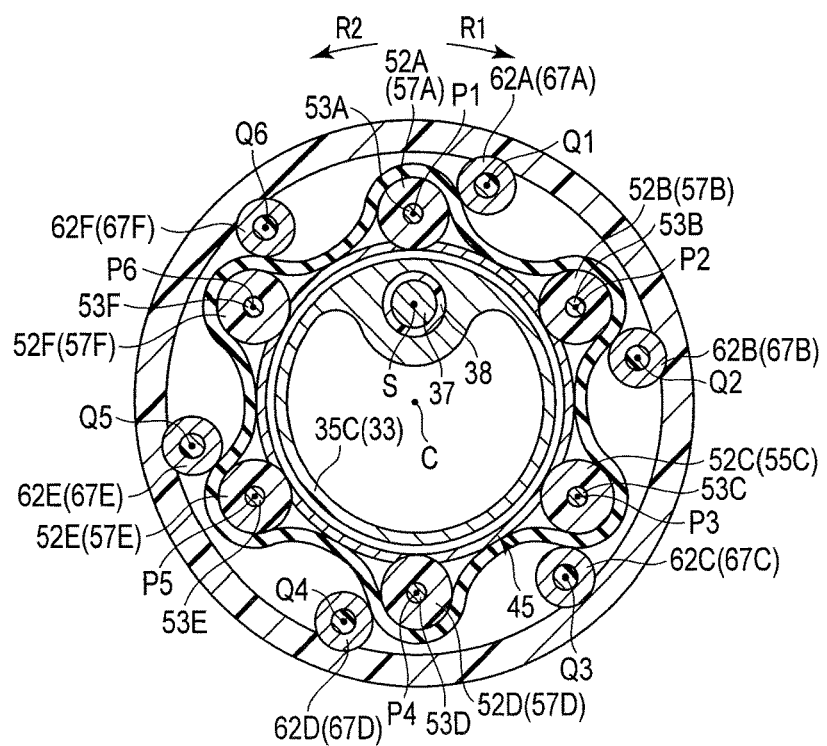
FIG. 4 is a sectional view taken along the line IV-IV in FIG. 2.

FIG. 3 is a sectional view taken along the line III-III in FIG. 2. FIG. 4 is a sectional view taken along the line IV-IV in FIG. 2. Therefore, FIG. 3 and FIG. 4 show the sections perpendicular to the longitudinal axis C. As shown in FIG. 2 to FIG. 4, a cavity 36 is formed by the base portion 33 in the insertion section 5. The cavity 36 is open toward the outer peripheral side at a first opening position E1, and open at a second opening position E2 toward the space where the imaging cable, the light guide (both are not shown), and others extend. In the cavity 36, a driving gear 37 is attached to the base portion 33 (coupling member 35C) via a support member 38. Inside the proximal side flexible tube section 32, a channel tube 41 extends from the proximal side to the distal side. The distal end of the channel tube 41 is connected to the base portion 33 (coupling member 35D) at the second opening position E2. Inside the channel tube 41, a driving shaft 42 extends along a shaft axis S which is substantially parallel to the longitudinal axis C. The distal end of the driving shaft 42 is inserted into the cavity 36 from the second opening position E2, and connected to the driving gear 37. The proximal end of the driving shaft 42 is coupled to the electric motor 25 via a gear (not shown) or the like. When the electric motor 25 is driven, driving force is transmitted to the driving shaft 42, and the driving shaft 42 rotates around the shaft axis S. As a result, the driving force is transmitted to the driving gear 37, and the driving gear 37 rotates.

The insertion section 5 includes a rotating tubular member 45 which is attached to the base portion 33 in a state to cover the base portion 33 (coupling member 35C) from the outer peripheral side. The rotating tubular member 45 is rotatable relative to the base portion 33 around the longitudinal axis C. An inner peripheral gear portion 46 is provided on the inner peripheral surface of the rotating tubular member 45. The inner peripheral gear portion 46 extends in all circumference around the longitudinal axis C. The driving gear 37 is in mesh with the inner peripheral gear portion 46 at the first opening position E1 of the cavity 36. Thus, the driving force is transmitted to the rotating tubular member 45 by the rotation of the driving gear 37, and the rotating tubular member 45 rotates around the longitudinal axis C. It is preferable that in the longitudinal direction along the longitudinal axis C, a space S'1 is formed between the distal end of the rotating tubular member 45 and the coupling member 35B, and a space S'2 is formed between the proximal end of the rotating tubular member 45 and the coupling member 35C. That is, it is preferable that both ends of the rotating tubular member 45 are located apart from the base portion 33 in the longitudinal direction. According to this configuration, the rotation of the rotating tubular member 45 around the longitudinal axis C is not prevented by the base portion 33.

Figure 5:
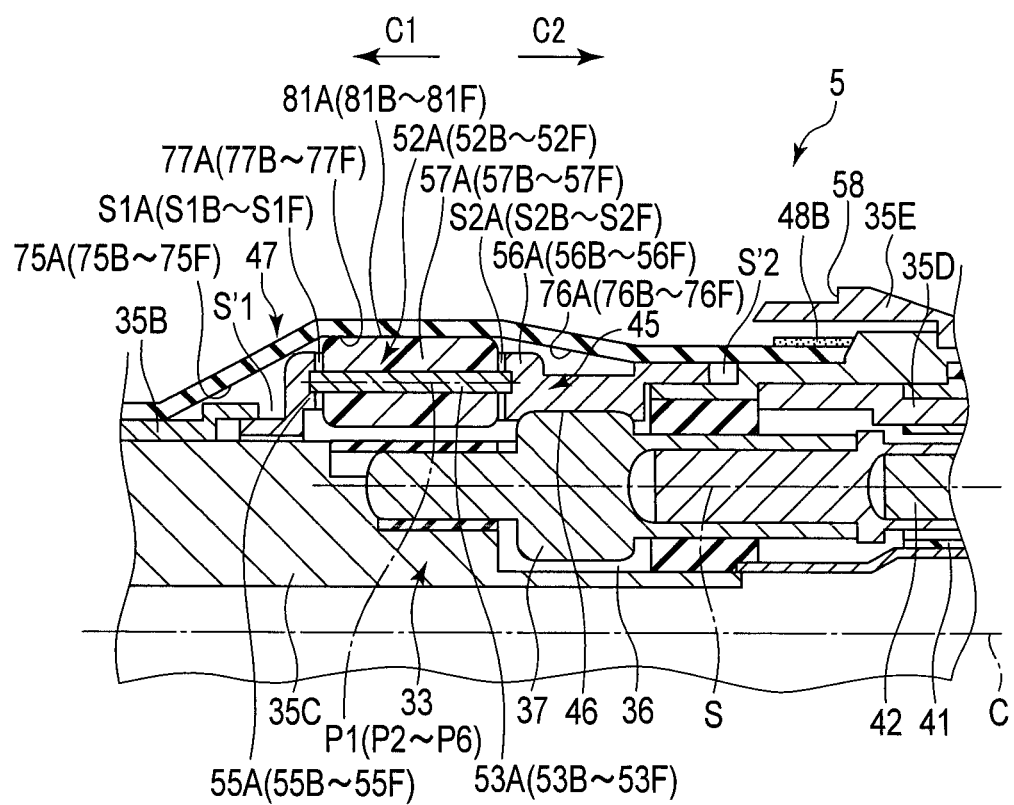
FIG. 5 is a sectional view schematically showing the configurations of a certain first roller and its vicinity in the insertion section, according to the first embodiment.

(In the present embodiment, six) first rollers (inner rollers) 52A to 52F are attached to the rotating tubular member 45. Each of the first rollers 52A to 52F is attached to the rotating tubular member 45 via the corresponding roller shaft (corresponding one of 53A to 53F). FIG. 5 is a view showing the configurations of a certain first roller (one of 52A to 52F) and its vicinity in the insertion section 5. FIG. 5 shows a section parallel to the longitudinal axis C, and does not show the spiral unit 20. As shown in FIG. 2 to FIG. 5, distal side shaft receivers 55A to 55F and proximal side shaft receivers 56A to 56F are formed in the rotating tubular member 45. To each of the distal side shaft receivers 55A to 55F, the distal end of the corresponding roller shaft (corresponding one of 53A to 53F) is connected. To each of the proximal side shaft receivers 56A to 56F, the proximal end of the corresponding roller shaft (corresponding one of 53A to 53F) is connected.

Each of the first rollers (rotating members) 52A to 52F has a first turning axis (corresponding one of P1 to P6) as a rotation axis, and is rotatable (turnable) relative to the rotating tubular member 45 around the first turning axis (corresponding one of P1 to P6). Here, each of the first turning axes (rotation axes) P1 to P6 is an axis different from the longitudinal axis C, and is defined to be substantially parallel to the longitudinal axis C by the corresponding roller shaft (corresponding one of 53A to 53F) in the present embodiment. Therefore, each of the first rollers (rotating members) 52A to 52F extends along the corresponding first turning axis (corresponding one of P1 to P6) from the proximal side to the distal side. On both sides of each of the first rollers 52A to 52F in a direction along the first turning axis (corresponding one of P1 to P6), the corresponding distal side shaft receiver (corresponding one of 55A to 55F) and the corresponding proximal side shaft receiver (corresponding one of 56A to 56F) are adjacently provided. That is, each of the distal side shaft receivers 55A to 55F and the proximal side shaft receivers 56A to 56F of the rotating tubular member 45 form adjacent portions adjacently provided on both sides of the corresponding first roller (corresponding one of 52A to 52F) in the direction along the first turning axis (corresponding one of P1 to P6). For example, the adjacent portions adjacently provided on both sides of the first roller 52A in the direction along the first turning axis P1 are formed by the distal side shaft receiver 55A and the proximal side shaft receiver 56A.

The first rollers 52A to 52F are provided apart from one another around the longitudinal axis C, and in the present embodiment, the first rollers 52A to 52F are arranged at substantially equal intervals around the longitudinal axis C. The rotating tubular member 45 and the first rollers 52A to 52F are rotatable (revolvable) around the longitudinal axis C together relative to the base portion 33. In each of the first rollers 52A to 52F, a first projection (corresponding one of 57A to 57F) protruding toward the outer peripheral side of the insertion section 5 relative to the corresponding distal side shaft receiver (corresponding one of 55A to 55F) and the corresponding proximal side shaft receiver (corresponding one of 56A to 56F) (i.e. relative to the adjacent portions) is formed as a protrusion. For example, in the first roller 52A, the first projection (protrusion) 57A protruding toward the outer peripheral side of the insertion section 5 relative to the distal side shaft receiver 55A and the proximal side shaft receiver 56A is formed.

In the insertion section 5, a cylindrical cover tube 47 which covers the rotating tubular member 45 and the first rollers 52A to 52F from the outer peripheral side is provided. The cover tube 47 is made of an elastic material such as rubber, and has a flexibility. A part of the outer surface of the insertion section 5 is formed by the cover tube 47. The distal end of the cover tube 47 is located on the distal side with respect to the distal end of the rotating tubular member 45, and fixed to the base portion 33 (coupling member 35B) by an adhesive member 48A. The proximal end of the cover tube 47 is located on the proximal side with respect to the proximal end of the rotating tubular member 45, and fixed to the base portion 33 (coupling member 35C) by an adhesive member 48B. At each of the distal and proximal ends of the cover tube 47, liquid tightness is maintained between the base portion 33 and the cover tube 47. This prevents the inflow of liquid from the outside of the insertion section 5 to the inner peripheral side of the cover tube 47, and prevents the inflow of liquid from the outside of the insertion section 5 to the cavity 36 where the driving gear 37 is disposed. The rotating tubular member 45 and the first rollers 52A to 52F are rotatable (revolvable) relative to the cover tube 47 around the longitudinal axis C.

The spiral unit (assistance tool) 20 is detachably attached to the insertion section 5 in a state where the proximal portion of the spiral unit 20 covers the cover tube 47 from the outer peripheral side. Therefore, in a state where the spiral unit (assistance tool) 20 is attached to the insertion section 5, the spiral unit 20 is located on the outer peripheral side with respect to the cover tube 47, and the rotating tubular member 45 and the first rollers 52A to 52F are located on the inner peripheral side with respect to the cover tube 47. Each of the first projections (protrusions) 57A to 57F presses the cover tube 47 from the inner peripheral side of the insertion section 5, and holds the cover tube 47 in an elastic deformation state. Thus, the cover tube 47 is provided in the insertion section 5 in the elastic deformation state, and protrudes toward the outer peripheral side of the insertion section 5 at a position (place) where the cover tube 47 is pressed from each of the first projections 57A to 57F.

In the coupling member 35E of the base portion 33, a receiving surface 58 on which a proximal end face 26 of the spiral unit 20 (a proximal end face of the tube main body 21)

can abut is formed. The receiving surface 58 is located on the proximal side with respect to the proximal end of the rotating tubular member 45. The proximal end face 26 of the spiral unit 20 abuts on the receiving surface 58, so that the movement of the spiral unit 20 toward the proximal side from the receiving surface 58 is prevented. An engagement groove 65 recessed toward the inner peripheral side is provided in the outer peripheral surface of the coupling member 35A of the base portion 33. The engagement groove 65 is located on the distal side with respect to the distal end of the rotating tubular member 45. The engagement groove 65 is formed in all circumference around the longitudinal axis C. An engagement claw 28 which protrudes toward the inner peripheral side is provided on the inner peripheral surface of the spiral unit 20 (the tube main body 21). When the spiral unit 20 is attached to the insertion section 5, the engagement claw 28 engages with the engagement groove 65. This regulates the movement of the spiral unit 20 relative to the insertion section 5 in the longitudinal direction along the longitudinal axis C. Since the movement of the spiral unit 20 relative to the insertion section 5 in the longitudinal direction is regulated, detachment of the spiral unit 20 from the insertion section 5 is prevented in a state where the spiral unit 20 is rotating around the longitudinal axis C by the transmission of driving force thereto.

(In the present embodiment, six) second rollers (outer rollers) 62A to 62F attached to the inner peripheral surface of the tube main body 21 are provided in the proximal portion of the spiral unit 20. The second rollers 62A to 62F are located on the proximal side with respect to the engagement claw 28. Each of the second rollers 62A to 62F has a second turning axis (corresponding one of Q1 to Q6), and is rotatable (turnable) relative to the tube main body 21 around the second turning axis (corresponding one of Q1 to Q6). In the present embodiment, each of the second turning axes Q1 to Q6 is defined to be substantially parallel to the longitudinal axis C. In the spiral unit (assistance tool) 20, each of the second rollers 62A to 62F forms a corresponding second projection (corresponding one of 67A to 67F). Each of the second projections (outer projections) 67A to 67F protrudes toward the inner peripheral side in the spiral unit 20.

The second rollers 62A to 62F (the second projections 67A to 67F) are provided apart from one another around the longitudinal axis C, and in the present embodiment, the second rollers 62A to 62F are arranged at substantially equal intervals around the longitudinal axis C. In a state where the spiral unit 20 is attached to the insertion section 5, each of the second rollers 62A to 62F (the second projections 67A to 67F) is disposed between corresponding two of the first rollers 52A to 52F (the first projections 57A to 57F) around the longitudinal axis C, and for example, the second roller 62A is disposed between the first roller 52A and the first rollers 52B around the longitudinal axis C.

When the driving force is transmitted to the rotating tubular member 45 as described above and the rotating tubular member 45 and the first rollers 52A to 52F rotate to one side (an arrow R1 side in each of FIGS. 3 and 4) around the longitudinal axis C, each of the first projections (protrusions) 57A to 57F applies press force to the corresponding second projection (corresponding one of 67A to 67F) in a rotation direction (in this case, clockwise around the longitudinal axis C in FIG. 4) via the cover tube 47. For example, the first projection 57A applies press force to the second projection 67A via the cover tube 47. Consequently, each of the second projections 67A to 67F of the spiral unit 20 receives the driving force from the corresponding first projection (corresponding one of 57A to 57F), and the spiral unit 20 rotates relative to the base portion 33 together with the rotating tubular member 45 and the first rollers 52A to 52F (the first projections 57A to 57F) toward one side around the longitudinal axis C. When the rotating tubular member 45 and the first rollers 52A to 52F rotate toward the other side (an arrow R2 side in each of FIGS. 3 and 4) around the longitudinal axis C, each of the first projections 57A to 57F applies press force to the corresponding second projection (corresponding one of 67A to 67F) different from that in the case where the rotating tubular member 45 rotates toward one side around the longitudinal axis C, in a rotation direction (in this case, counterclockwise around the longitudinal axis C in FIG. 4) via the cover tube 47. For example, the first projection 57A applies press force to the second projection 67F via the cover tube 47. Consequently, each of the second projections 67A to 67F receives the driving force from the corresponding first projection (corresponding one of 57A to 57F), and the spiral unit 20 rotates relative to the base portion 33 together with the rotating tubular member 45 and the first rollers 52A to 52F toward the other side around the longitudinal axis C.

When the spiral unit 20 rotates around the longitudinal axis C in a state where the spiral fin 22 is pressed to the inner peripheral side, propulsive force toward the distal side or the proximal side (one side in the longitudinal direction) is applied to the insertion section 5 and the spiral unit 20. In a state where the rotating tubular member 45 and the spiral unit 20 rotate together, the cover tube 47 does not rotate.

FIG. 6 is a diagram illustrating a state (natural state) where the cover tube 47 is not elastically deformed, and a state where the cover tube 47 is elastically deformed by pressure from each of the first projections (protrusions) 57A to 57F. As shown in FIG. 6, the cover tube 47 which is not in the elastic deformation state includes a distal side tubular portion 71 which forms the distal end of the cover tube 47, and a proximal side tubular portion 72 which forms the proximal end of the cover tube 47 and which is provided on the proximal side with respect to the distal side tubular portion 71. In each of the distal side tubular portion 71 and the proximal side tubular portion 72, the diameter thereof is uniform over the entire length in a direction along the longitudinal axis C, and the diameter is larger in the proximal side tubular portion 72 than in the distal side tubular portion 71. Here, the case where the diameter is uniform over the entire length in the direction along the longitudinal axis C includes the case where the diameter changes within a slight range alone and the diameter hardly changes over the entire length in the direction along the longitudinal axis C as well as the case where the diameter is the same over the entire length in the direction along the longitudinal axis C. In the cover tube 47 which is not in the elastic deformation state (natural state), an intermediate taper portion 73 extends (is continuous) between the distal side tubular portion 71 and the proximal side tubular portion 72. In the intermediate taper portion 73, the diameter increases from the distal side toward the proximal side.

As shown in FIG. 5 and FIG. 6, in a state where the cover tube 47 is elastically deformed by pressure from the first projections 57A to 57F, the distal end of each of the first projections 57A to 57F is in abutment with the inner peripheral surface of the cover tube 47 at a boundary position between the proximal side tubular portion 72 and the intermediate taper portion 73, and presses the cover tube 47 at the boundary position between the proximal side tubular portion 72 and the intermediate taper portion 73. The proximal end of each of the first projections 57A to 57F is in abutment with the inner peripheral surface of the cover tube 47 in the proximal side tubular portion 72, and presses the cover tube 47 in the proximal side tubular portion 72. In the cover tube 47 provided in the insertion section 5, the proximal side tubular portion 72 and the intermediate taper portion 73 are elastically deformed from the natural state by pressure force from the first projections 57A to 57F. Due to the elastic deformation of the cover tube 47, the part of the cover tube 47 pressed to the outer peripheral side from each of the first projections 57A to 57F is moved to the outer peripheral side as compared to the natural state. Thus, elastic force to restore to the natural state is generated in the cover tube 47, and the elastic force by the cover tube 47 is applied to each of the first projections (protrusions) 57A to 57F from the outer peripheral side toward the inner peripheral side.

In a state where the cover tube 47 is elastically deformed by pressure from each of the first projections (protrusions) 57A to 57F in the insertion section 5, distal side dimension changing portions (distal side dimension changing surfaces) 75A to 75F, proximal side dimension changing portions (proximal dimension changing surfaces) 76A to 76F, and dimensionally uniform intermediate portions (dimensionally uniform intermediate surfaces) 77A to 77F are formed on the inner peripheral surface of the cover tube 47. Each of the distal side dimension changing portions 75A to 75F is formed toward the distal side from a pressure position (corresponding one of Z1A to Z1F) by the distal end of the corresponding first projection (corresponding one of 57A to 57F), and decreases in dimension in a diametrical direction from the longitudinal axis C from the proximal side toward the distal side. In the present embodiment, the distal side dimension changing portions 75A to 75F are formed by the elastic deformation of the intermediate taper portion 73 from the natural state. The pressure positions Z1A to Z1F are located at the boundary position between the proximal side tubular portion 72 and the intermediate taper portion 73 in the natural state of the cover tube 47, and the distal side dimension changing portions 75A to 75F extend toward the distal side from the boundary position between the proximal side tubular portion 72 and the intermediate taper portion 73 in the natural state of the cover tube 47.

Each of the proximal side dimension changing portions 76A to 76F is formed toward the proximal side from a pressure position (corresponding one of Z2A to Z2F) by the proximal end of the corresponding first projection (corresponding one of 57A to 57F), and decreases in dimension in the diametrical direction from the longitudinal axis C from the distal side toward the proximal side. In the present embodiment, the proximal side dimension changing portions 76A to 76F are formed by the elastic deformation of the proximal side tubular portion 72 from the natural state. The pressure positions Z2A to Z2F are located within a range in which the proximal side tubular portion 72 extends in the natural state of the cover tube 47.

Each of the dimensionally uniform intermediate portions 77A to 77F extends along the longitudinal axis C (the first turning axis (corresponding one of P1 to P6) of the corresponding first projection (corresponding one of 57A to 57F)) between the corresponding distal side dimension changing portion (corresponding one of 75A to 75F) and the corresponding proximal side dimension changing portion (corresponding one of 76A to 76F). In each of the dimensionally uniform intermediate portions 77A to 77F, the dimension in the diametrical direction from the longitudinal axis C is uniform over the entire length in the direction along the longitudinal axis C. Here, the case where the dimension is uniform over the entire length in the direction along the longitudinal axis C includes the case where the dimension changes within a slight range alone and the dimension hardly changes over the entire length in the direction along the longitudinal axis C as well as the case where the dimension is the same over the entire length in the direction along the longitudinal axis C. With each of the dimensionally uniform intermediate portions 77A to 77F, a protruding end face (corresponding one of 81A to 81F) of the corresponding first projection (corresponding one of 57A to 57F) toward the outer peripheral side is in abutment. In the cover tube 47, each of the dimensionally uniform intermediate portions 77A to 77F is continuous between the pressure position (corresponding one of Z1A to Z1F) by the distal end of the corresponding first projection (corresponding one of 57A to 57F) and the pressure position (corresponding one of Z2A to Z2F) by the proximal end of the corresponding first projection (corresponding one of 57A to 57F). In the present embodiment, the dimensionally uniform intermediate portions 77A to 77F are formed by the elastic deformation of the proximal side tubular portion 72 from the natural state. The dimensionally uniform intermediate portions 77A to 77F extends toward the proximal side from the boundary position between the proximal side tubular portion 72 and the intermediate taper portion 73 in the natural state of the cover tube 47.

In the present embodiment, the position of each of the first rollers (rotating members) 52A to 52F in a direction along the first turning axis (corresponding one of P1 to P6) is adjusted by the elastic force from the cover tube 47 elastically deformed by the pressure from the first projections 57A to 57F. In the insertion section 5, the movement range of each of the first rollers 52A to 52F in the direction (longitudinal direction) along the first turning axis (corresponding one of P1 to P6) is regulated by the corresponding distal side dimension changing portion (corresponding one of 75A to 75F) and the corresponding proximal side dimension changing portion (corresponding one of 76A to 76F) of the cover tube 47, and the position of each of the first rollers 52A to 52F relative to the adjacent portions (corresponding one of 55A to 55F and corresponding one of 56A to 56F) in the direction along the first turning axis (corresponding one of P1 to P6) is adjusted. In the insertion section 5, the position of each of the first rollers 52A to 52F in the direction along the first turning axis (corresponding one of P1 to P6) is adjusted, so that a space (corresponding one of S1A to S1F) is formed between the distal end of each of the first rollers 52A to 52F and the corresponding distal side shaft receiver (corresponding one of 55A to 55F), and a space (corresponding one of S2A to S2F) is formed between the proximal end of each of the first rollers 52A to 52F and the corresponding proximal side shaft receiver (corresponding one of 56A to 56F). Therefore, in the insertion section 5, both ends of each of the first rollers (rotating members) 52A to 52F in the direction along the first turning axis (corresponding one of P1 to P6) are maintained (held) in a state to be located apart from the adjacent portions (corresponding one of 55A to 55F and corresponding one of 56A to 56F).

Next, functions and advantageous effects of the endoscope device 2 which is the insertion device according to the present embodiment are described. When a lumen is observed by use of the endoscope device 2, the spiral unit (assistance tool) 20 is attached to the insertion section 5, and the insertion section 5 and the spiral unit 20 are inserted into the lumen. On the basis of an operation input in the operation input device 14, the electric motor 25 is driven, and driving force is transmitted to the spiral unit 20 as described above. As a result, the spiral unit 20 rotates around the longitudinal axis (revolution axis) C. When the spiral unit 20 rotates in a state where the spiral fin 22 is pressed to the inner peripheral side by a luminal wall, propulsive force toward the distal side or the proximal side (one side in a direction parallel to the longitudinal axis C) is applied to the insertion section 5 and the spiral unit 20. Mobility of the insertion section 5 in the lumen is improved by the propulsive force.

In the insertion section 5 according to the present embodiment, both ends of each of the first rollers (rotating members) 52A to 52F in the direction along the first turning axis (corresponding one of P1 to P6) are maintained (held) by the cover tube 47 in a state to be located apart from the adjacent portions (corresponding one of 55A to 55F and corresponding one of 56A to 56F). Each of the first rollers 52A to 52F is adjusted to a position out of contact with the adjacent portions (corresponding one of 55A to 55F and corresponding one of 56A to 56F) in the direction along the first turning axis (corresponding one of P1 to P6), whereby the rotation (turning) of each of the first rollers 52A to 52F around the first turning axis (corresponding one of P1 to P6) is not prevented. Thus, in a state where the first rollers 52A to 52F and the rotating tubular member 45 rotate (revolve) relative to the base portion 33 around the longitudinal axis C, each of the first rollers 52A to 52F appropriately rotates (turns) relative to the rotating tubular member 45 around the first turning axis (corresponding one of P1 to P6), and friction between each of the first projections 57A to 57F and the cover tube 47 is lower. Accordingly, the rotation (revolution) of the first rollers 52A to 52F and the rotating tubular member 45 around the longitudinal axis C is not disturbed by the cover tube 47, and the first rollers 52A to 52F and the rotating tubular member 45 appropriately rotate around the longitudinal axis C. As a result, press force is appropriately applied to the second projections 67A to 67F of the spiral unit 20, and the spiral unit 20 appropriately rotates around the longitudinal axis C. In this instance, because each of the second rollers 62A to 62F turns (rotates) around the second turning axis (corresponding one of Q1 to Q6), friction between each of the second projections 67A to 67F and the cover tube 47 is also lower.

In the present embodiment, in the natural state where the cover tube 47 is not elastically deformed, the cover tube 47 includes the distal side tubular portion 71, the proximal side tubular portion 72, and the intermediate taper portion 73. Owing to this configuration, in a state where the cover tube 47 is elastically deformed by the pressure from each of the first projections (protrusions) 57A to 57F, the distal side dimension changing portions 75A to 75F and the proximal side dimension changing portions 76A to 76F are more easily formed in the cover tube 47. That is, in the state where the cover tube 47 is elastically deformed, the configuration to adjust the position of each of the first projections 57A to 57F in the direction along the first turning axis (corresponding one of P1 to P6) is more easily formed in the cover tube 47. Moreover, in the present embodiment, each of the first projections 57A to 57F is disposed in a state where the distal end of each of the first projections (protrusions) 57A to 57F presses the boundary position between the proximal side tubular portion 72 and the intermediate taper portion 73, so that in the cover tube 47, toward the distal side from the pressure position (corresponding one of Z1A to Z1F) by the distal end of each of the first projections 57A to 57F, the corresponding distal side dimension changing portion (corresponding one of 75A to 75F) is more easily formed.

When the spiral unit 20 is attached to the insertion section 5, the insertion section 5 is inserted into the spiral unit 20 from the distal end, and the spiral unit 20 is moved toward the proximal side relative to the insertion section 5 along the longitudinal axis C. Thus, in the insertion section 5, the diameter (outside diameter) is larger in the proximal side flexible tube section 32 than in the distal side flexible tube section 31, and the diameter (outside diameter) is larger in a part (e.g. the coupling member 35E) located on the proximal side with respect to the rotating tubular member 45, than in a part (e.g. the coupling member 35B) located on the distal side with respect to the rotating tubular member 45. In the present embodiment, in the cover tube 47 in the natural state which is not elastically deformed, the distal end is formed by the distal side tubular portion 71 which is small in diameter, and the proximal end is formed by the proximal side tubular portion 72 which is large in diameter. Thus, at the time of the manufacture of the insertion section 5, the distal end of the cover tube 47 is more easily fixed to the small-diameter part of the base portion 33 located on the distal side with respect to the rotating tubular member 45, and the proximal end of the cover tube 47 is more easily fixed to the large-diameter part of the base portion 33 located on the proximal side with respect to the rotating tubular member 45.

Modifications of First Embodiment

Figure 7:
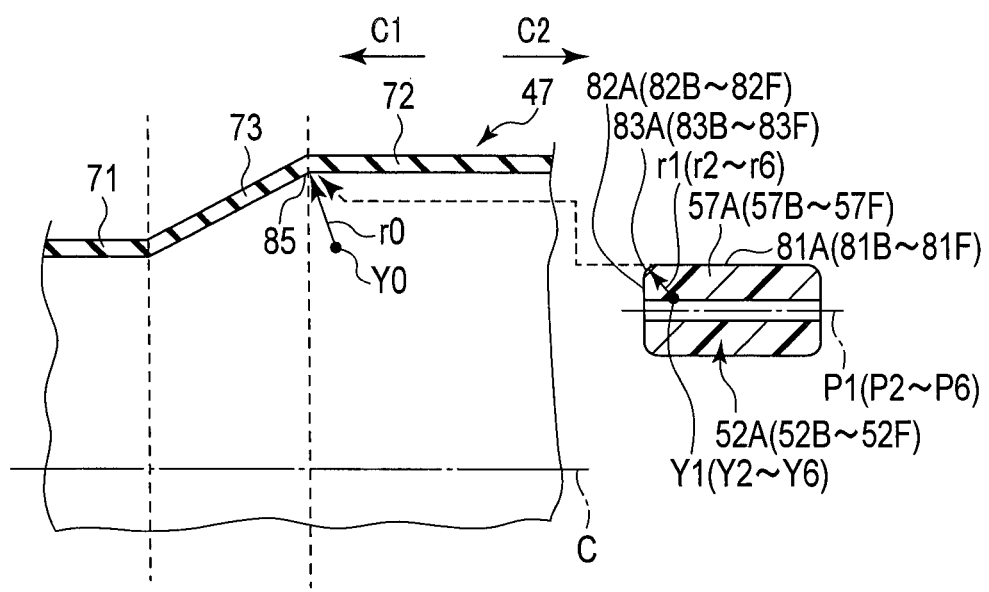
FIG. 7 is a schematic diagram showing the configurations of the cover tube and a certain first roller according to a first modification of the first embodiment.

In a first modification of the first embodiment shown in FIG. 7, an inner peripheral curved surface 85 is formed in the inner peripheral surface of the cover tube 47. The inner peripheral curved surface 85 is provided at the boundary position between the proximal side tubular portion 72 and the intermediate taper portion 73. In each of the first rollers 52A to 52F, the distal end of the first projection (corresponding one of 57A to 57F) abuts on the inner peripheral curved surface 85, and presses the cover tube 47 toward the outer peripheral side of the insertion section 5 in the inner peripheral curved surface 85. Each of the first projections 57A to 57F has the protruding end face (corresponding one of 81A to 81F) facing toward the outer peripheral side of the insertion section 5, and projecting distal end face (corresponding one of 82A to 82F) facing toward the distal side. In the outer surface of each of the first projections 57A to 57F, projecting curved surface (corresponding one of 83A to 83F) is continuous between the protruding end face (corresponding one of 81A to 81F) and the projecting distal end face (corresponding one of 82A to 82F). In each of the first projections 57A to 57F, a part of the distal end is formed by the projecting curved surface (corresponding one of 83A to 83F). In each of the first projections 57A to 57F, in a section parallel to the first turning axis (corresponding one of P1 to P6), the projecting curved surface (corresponding one of 83A to 83F) is formed into an arc shape having a first curvature radius (corresponding one of r1 to r6), and a center (corresponding one of Y1 to Y6) of the arc is located on the inner peripheral side of the insertion section 5 with respect to the protruding end face (corresponding one of 81A to 81F).

In the cover tube 47, in a section parallel to the longitudinal axis C, the inner peripheral curved surface 85 provided at the boundary position between the proximal side tubular portion 72 and the intermediate taper portion 73 is formed into an arc shape having a second curvature radius r0, and a center Y0 of the arc is located on the inner peripheral side with respect to the cover tube 47. In the insertion section 5, the projecting curved surface (corresponding one of 83A to 83F) of each of the first projections 57A to 57F abuts on the inner peripheral curved surface 85, and presses the cover tube 47 in the inner peripheral curved surface 85. The distal end (the projecting curved surface (corresponding one of 83A to 83F)) of each of the first projections 57A to 57F abuts on the cover tube 47 in the inner peripheral curved surface 85 which is in a curved surface shape, whereby in a state where the cover tube 47 is elastically deformed by the pressure from the first projections 57A to 57F, concentration of force at the boundary position between the proximal side tubular portion 72 and the intermediate taper portion 73 is prevented. The force applied to the cover tube 47 is dispersed in a state where the cover tube 47 is elastically deformed by the pressure from the first projections 57A to 57F, so that the durability of the cover tube 47 is improved.

It is preferable that the second curvature radius r0 of the arc of the inner peripheral curved surface 85 of the cover tube 47 is larger than the first curvature radius (corresponding one of r1 to r6) of the arc of the projecting curved surface (corresponding one of 83A to 83F) of each of the first projections 57A to 57F. This more effectively prevents the concentration of force at the boundary position between the proximal side tubular portion 72 and the intermediate taper portion 73 in a state where the cover tube 47 is elastically deformed by the pressure from the first projections 57A to 57F, and further improves the durability of the cover tube 47.

Figure 8:
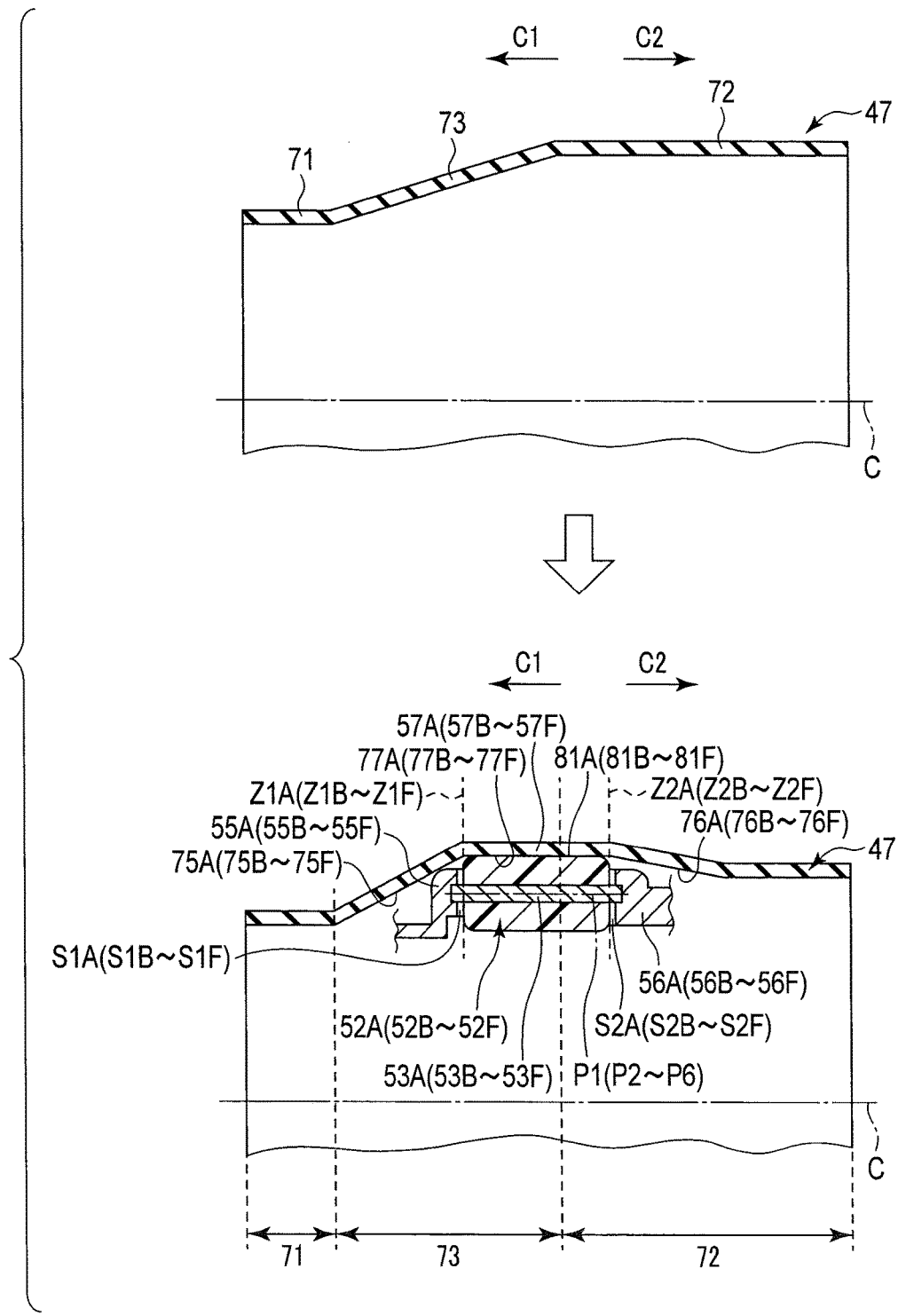
FIG. 8 is a schematic diagram illustrating a state where the cover tube is not elastically deformed, and a state where the cover tube is elastically deformed by the pressure from each of the first projections, according to a second modification of the first embodiment.

In a second modification of the first embodiment shown in FIG. 8, in a state where the cover tube 47 is elastically deformed by the pressure from the first projections 57A to 57F, the distal end of each of the first projections 57A to 57F presses the cover tube 47 in the intermediate taper portion 73, and the proximal end of each of the first projections 57A to 57F presses the cover tube 47 in the proximal side tubular portion 72. Thus, the pressure position (corresponding one of Z1A to Z1F) by the distal end of each of the first projections 57A to 57F is located within a range in which the intermediate taper portion 73 extends in the natural state of the cover tube 47. The pressure position (corresponding one of Z2A to Z2F) by the proximal end of each of the first projections 57A to 57F is located within a range in which the proximal side tubular portion 72 extends in the natural state of the cover tube 47.

In the present modification, the distal side dimension changing portions 75A to 75F are formed by the elastic deformation of the intermediate taper portion 73, and the proximal side dimension changing portions 76A to 76F are formed by the elastic deformation of the proximal side tubular portion 72. The dimensionally uniform intermediate portions 77A to 77F are formed by the elastic deformation of the proximal side tubular portion 72 and the intermediate taper portion 73. Therefore, each of the dimensionally uniform intermediate portions 77A to 77F extends through the boundary position between the proximal side tubular portion 72 and the intermediate taper portion 73 in the natural state of the cover tube 47.

In the present modification as well, each of the distal side dimension changing portions 75A to 75F is formed toward the distal side from the pressure position (corresponding one of Z1A to Z1F) by the distal end of the corresponding first projection (corresponding one of 57A to 57F), and each of the proximal side dimension changing portions 76A to 76F is formed toward the proximal side from the pressure position (corresponding one of Z2A to Z2F) by the proximal end of the corresponding first projection (corresponding one of 57A to 57F). Therefore, as in the first embodiment, the position of each of the first rollers 52A to 52F relative to the adjacent portions (corresponding one of 55A to 55F and corresponding one of 56A to 56F) in the direction along the first turning axis (corresponding one of P1 to P6) is adjusted by the elastic force from the cover tube 47 and by the corresponding distal side dimension changing portion (corresponding one of 75A to 75F) and the corresponding proximal side dimension changing portion (corresponding one of 76A to 76F). Therefore, in the insertion section 5 according to the present modification as well, each of the first rollers (rotating members) 52A to 52F is maintained (held) by the cover tube 47 in a state where both ends thereof in the direction along the first turning axis (corresponding one of P1 to P6) are located apart from the adjacent portions (corresponding one of 55A to 55F and corresponding one of 56A to 56F). Consequently, functions and advantageous effects similar to those in the first embodiment are provided in the present modification as well.

In the present modification, each of the first projections (protrusions) 57A to 57F is disposed in a state where the distal end of each of the first projections 57A to 57F presses the intermediate taper portion 73, so that in the cover tube 47, toward the distal side from the pressure position (corresponding one of Z1A to Z1F) by the distal end of each of the first projections 57A to 57F, the corresponding distal side dimension changing portion (corresponding one of 75A to 75F) is more easily formed.

In a third modification of the first embodiment shown in FIG. 9, in a state where the cover tube 47 is elastically deformed by the pressure from the first projections 57A to 57F, both the distal end and proximal end of each of the first projections 57A to 57F press the cover tube 47 in the intermediate taper portion 73. Thus, the pressure position (corresponding one of Z1A to Z1F) by the distal end of each of the first projections 57A to 57F and the pressure position (corresponding one of Z2A to Z2F) by the proximal end of each of the first projections 57A to 57F are located within a range in which the intermediate taper portion 73 extends in the natural state of the cover tube 47. In the present modification, the distal side dimension changing portions 75A to 75F, the proximal side dimension changing portions 76A to 76F, and the dimensionally uniform intermediate portions 77A to 77F are formed by the elastic deformation of the intermediate taper portion 73.

In the present modification as well, each of the distal side dimension changing portions 75A to 75F is formed toward the distal side from the pressure position (corresponding one of Z1A to Z1F) by the distal end of the corresponding first projection (corresponding one of 57A to 57F), and each of the proximal side dimension changing portions 76A to 76F is formed toward the proximal side from the pressure position (corresponding one of Z2A to Z2F) by the proximal end of the corresponding first projection (corresponding one of 57A to 57F). Therefore, as in the embodiment and others described above, the position of each of the first rollers 52A to 52F relative to the adjacent portions (corresponding one of 55A to 55F and corresponding one of 56A to 56F) in the direction along the first turning axis (corresponding one of P1 to P6) is adjusted by the elastic force from the cover tube 47 and by the corresponding distal side dimension changing portion (corresponding one of 75A to 75F) and the corresponding proximal side dimension changing portion (corresponding one of 76A to 76F). Therefore, in the insertion section 5 according to the present modification as well, each of the first rollers (rotating members) 52A to 52F is maintained (held) by the cover tube 47 in a state where both ends thereof in the direction along the first turning axis (corresponding one of P1 to P6) are located apart from the adjacent portions (corresponding one of 55A to 55F and corresponding one of 56A to 56F). Consequently, functions and advantageous effects similar to those in the embodiment and others described above are provided in the present modification as well.

In an unshown certain modification, the cover tube 47 may be formed uniformly in diameter over the entire length in the longitudinal direction in the state (natural state) where the cover tube 47 is not elastically deformed. In this case, the distal side tubular portion 71, the proximal side tubular portion 72, and the intermediate taper portion 73 are not formed in the cover tube 47 in the natural state.

However, in the present modification as well, each of the distal side dimension changing portions 75A to 75F is formed toward the distal side from the pressure position (corresponding one of Z1A to Z1F) by the distal end of the corresponding first projection (corresponding one of 57A to 57F), and each of the proximal side dimension changing portions 76A to 76F is formed toward the proximal side from the pressure position (corresponding one of Z2A to Z2F) by the proximal end of the corresponding first projection (corresponding one of 57A to 57F). Therefore, as in the embodiment and others described above, the position of each of the first rollers 52A to 52F relative to the adjacent portions (corresponding one of 55A to 55F and corresponding one of 56A to 56F) in the direction along the first turning axis (corresponding one of P1 to P6) is adjusted by the elastic force from the cover tube 47 and by the corresponding distal side dimension changing portion (corresponding one of 75A to 75F) and the corresponding proximal side dimension changing portion (corresponding one of 76A to 76F). Therefore, in the insertion section 5 according to the present modification as well, each of the first rollers (rotating members) 52A to 52F is maintained (held) by the cover tube 47 in a state where both ends thereof in the direction along the first turning axis (corresponding one of P1 to P6) are located apart from the adjacent portions (corresponding one of 55A to 55F and corresponding one of 56A to 56F). Consequently, functions and advantageous effects similar to those in the embodiment and others described above are provided in the present modification as well.

Second Embodiment

Next, a second embodiment of the present invention is described with reference to FIG. 10 to FIG. 12. The second embodiment is the following modification of the configuration according to the first embodiment. The same parts as those in the first embodiment are denoted by the same reference signs and are not described.

Figure 10:
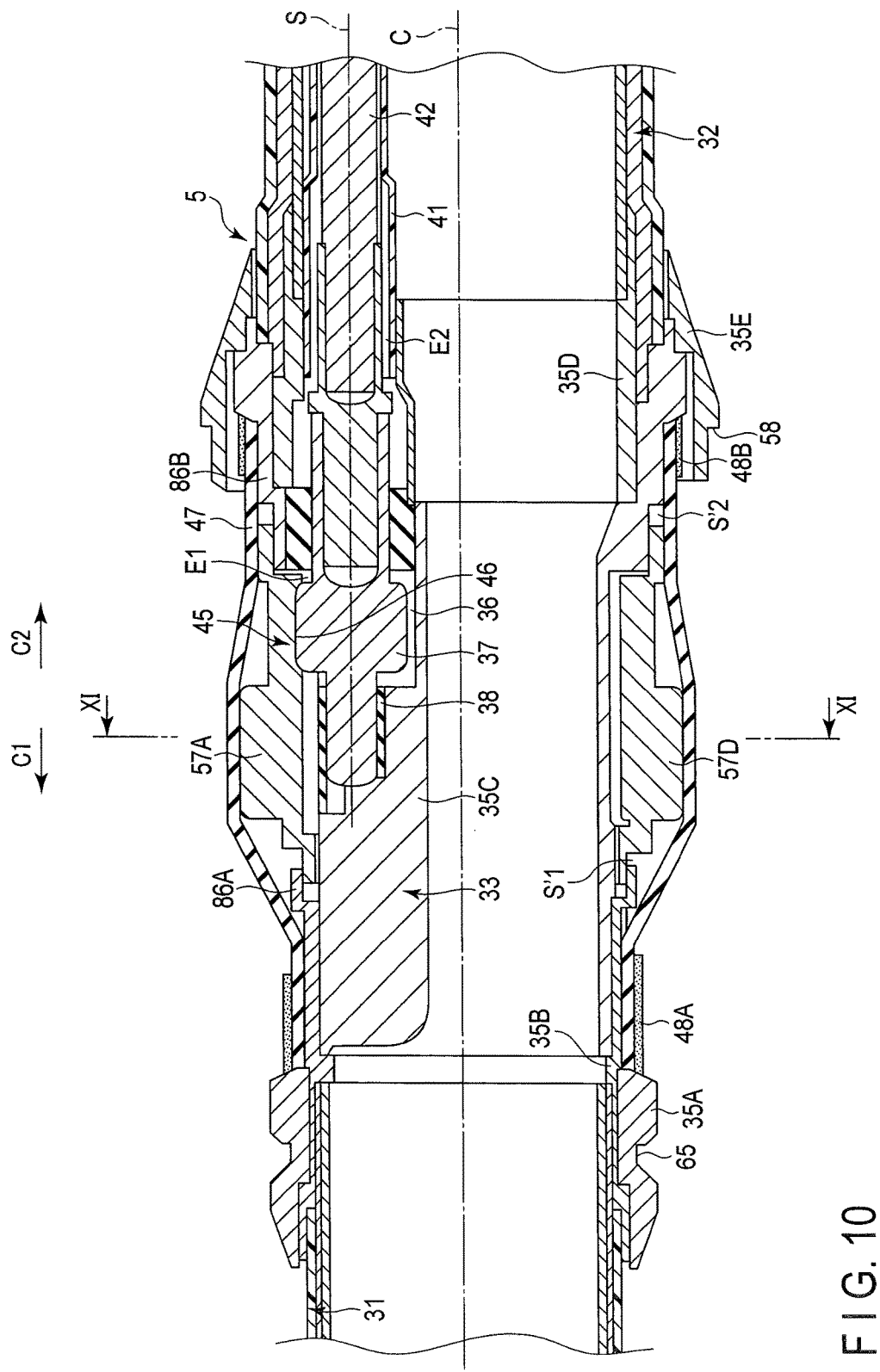
FIG. 10 is a sectional view schematically showing the configuration of the insertion section in the attachment part in which the spiral unit is attached to the insertion section and in the vicinity of the attachment part, according to the second embodiment.
Figure 11:
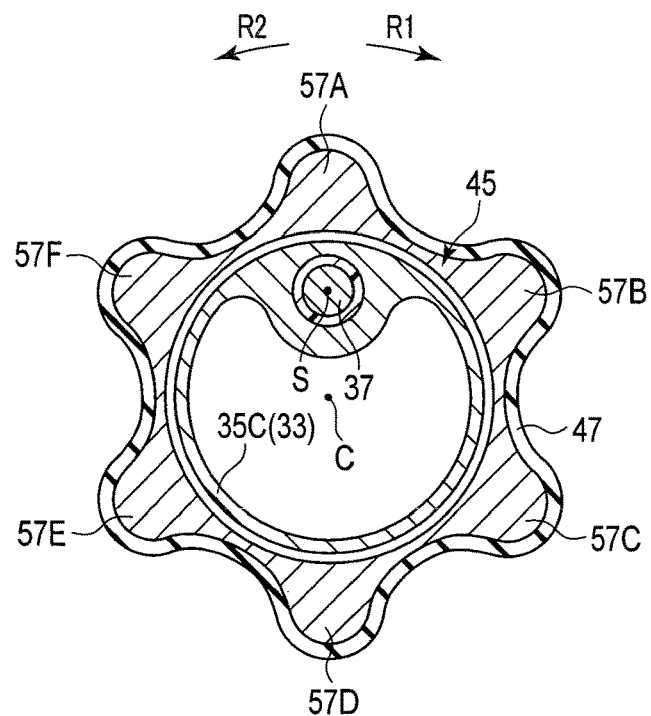
FIG. 11 is a sectional view taken along the line XI-XI in FIG. 10.

FIG. 10 is a view showing the configuration of the insertion section 5 in the attachment part in which the spiral unit 20 is attached to the insertion section 5 and in the vicinity of this part. FIG. 11 is a sectional view taken along the line XI-XI in FIG. 10. As shown in FIG. 10 and FIG. 11, in the present embodiment, the first rollers 52A to 52B and the roller shafts 53A to 53F are not provided. However, in the present modification as well, the rotating tubular member (rotating member) 45 which is rotatable relative to the base portion 33 around the longitudinal axis C as a rotation axis is provided in the insertion section 5.

A distal side adjacent portion 86A is formed on the distal side of the rotating tubular member 45 by the coupling member 35B of the base portion 33. A proximal side adjacent portion 86B is formed on the proximal side of the rotating tubular member 45 by the coupling member 35C. That is, the adjacent portions (86A and 86B) are formed on both sides of the rotating tubular member 45 in the direction (longitudinal direction) along the longitudinal axis C. In the present embodiment, the first projections 57A to 57F which protrude toward the outer peripheral side of the insertion section 5 relative to the distal side adjacent portion 86A and the proximal side adjacent portion 86B are formed as protrusions in the rotating tubular member 45. In the present embodiment as well, the first projections 57A to 57F are provided apart from one another around the longitudinal axis C.

In the present embodiment as well, in a state where the spiral unit 20 is attached to the insertion section 5, each of the first projections (protrusions) 57A to 57F applies press force to the corresponding second projection (corresponding one of 67A to 67F) in the rotation direction via the cover tube 47 when the rotating tubular member 45 rotates around the longitudinal axis C. Consequently, each of the second projections 67A to 67F of the spiral unit 20 receives driving force from the corresponding first projection (corresponding one of 57A to 57F), and the spiral unit 20 rotates relative to the base portion 33 together with the rotating tubular member 45 around the longitudinal axis C.

Figure 12:
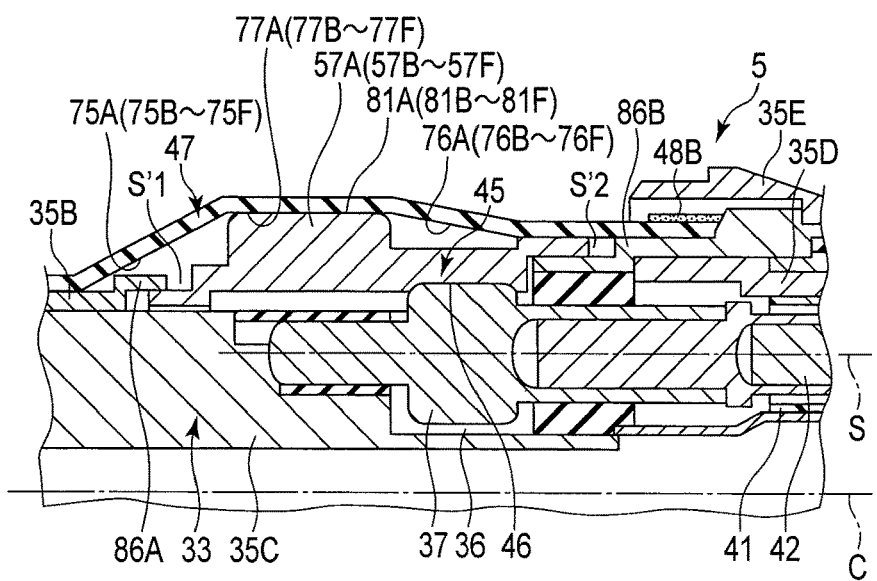
FIG. 12 is a sectional view schematically showing the configurations of a certain first projection and its vicinity in the insertion section according to the second embodiment.

FIG. 12 is a view showing the configurations of a certain first projection (one of 57A to 57F) and its vicinity in the insertion section 5. FIG. 12 shows a section parallel to the longitudinal axis C, and does not show the spiral unit 20. As shown in FIG. 10 to FIG. 12, in the present embodiment as well, in the insertion section 5, the cover tube 47 is elastically deformed from the natural state by the pressure from the first projections 57A to 57F. In a state where the cover tube 47 is elastically deformed by the pressure from the first projections 57A to 57F, the distal side dimension changing portions (distal side dimension changing surfaces) 75A to 75F, the proximal side dimension changing portions (proximal dimension changing surfaces) 76A to 76F, and the dimensionally uniform intermediate portions (dimensionally uniform intermediate surfaces) 77A to 77F are formed in the cover tube 47, as in the first embodiment described above.

In the present embodiment as well, the movement range of each of the first projections 57A to 57F in the direction along the longitudinal axis (rotation axis) C is regulated by the elastic force from the cover tube 47 and by the corresponding distal side dimension changing portion (corresponding one of 75A to 75F) and the corresponding proximal side dimension changing portion (corresponding one of 76A to 76F). Accordingly, the movement range of the rotating tubular member 45 in the direction (longitudinal direction) along the longitudinal axis C is regulated, and the position of the rotating tubular member 45 relative to the adjacent portions (86A and 86B) in the longitudinal direction is adjusted. In the insertion section 5, the position of the rotating tubular member 45 in the direction along the longitudinal axis C is adjusted, so that the space S'1 is formed between the distal end of the rotating tubular member 45 and the distal side adjacent portion 86A, and the space S'2 is formed between the proximal end of the rotating tubular member 45 and the proximal side adjacent portion 86B. Therefore, in the insertion section 5, the rotating tubular member 45 is maintained (held) by the cover tube 47 in a state where both ends thereof in the direction along the longitudinal axis (rotation axis) C are located apart from the adjacent portions (86A and 86B).

As described above, in the present embodiment, the rotating tubular member 45 is adjusted to the position out of contact with the adjacent portions (86A and 86B) in the direction along the longitudinal axis C, so that the rotation of the rotating tubular member 45 around the longitudinal axis C is not prevented. Thus, the rotating tubular member 45 is appropriately rotated by the transmission of driving force thereto. As a result, press force is appropriately applied to the second projections 67A to 67F of the spiral unit 20, and the spiral unit 20 appropriately rotates around the longitudinal axis C.

Modification of Second Embodiment

In the second embodiment as well, as has been described above in the modifications of the first embodiment, the configurations of the first projections (protrusions) 57A to 57F and the configuration of the cover tube 47 which is not in the elastic deformation state (natural state) may be modified.

Other Modifications

Although the corresponding second projection (corresponding one of 67A to 67F) is formed in each of the second rollers 62A to 62F in the spiral unit 20 in the embodiments and others described above, this is not a limitation. For example, in a certain modification, no turnable rollers are provided in the spiral unit 20, and the second projections 67A to 67F are formed integrally with the tube main body 21.

The number of the first projections (inner projections) 57A to 57F and the number of the second projections (outer projections) 67A to 67F are not limited to those in the embodiments described above. In a certain modification, the insertion section 5 may be provided with three first projections (e.g. 57A to 57C) at substantially equal intervals around the longitudinal axis C, or may be provided with only one first projection (57A). Similarly, the spiral unit 20 may be provided with three second projections (e.g. 67A to 67C) at substantially equal intervals around the longitudinal axis C, or may be provided with only one second projection (67A). The spiral unit (20) which is the assistance tool has only to rotate around the longitudinal axis C when press force is applied from each of the first projections (57A to 57F; 57A to 57C; 57A) to the corresponding second projection (corresponding one of 67A to 67F; corresponding one of 67A to 67C; 67A) by the rotation of the rotating tubular member (45) and the first projections (57A to 57F; 57A to 57C; 57A).

Although the spiral unit (20) is described by way of example as the assistance tool which is attached to the insertion section (5) in the embodiments and others described above, the assistance tool is not limited to the spiral unit (20). Although the endoscope (3) is described by way of example as the insertion instrument in the embodiments and others described above, the insertion instrument is not limited to the endoscope (3). For example, the configuration described above may be applied to an insertion surgical system in which a manipulator is used as the insertion instrument.

In the embodiments and others described above, the insertion instrument (3) includes the insertion section (5) extending from the proximal side to the distal side along the longitudinal axis (C), the rotating member (52A to 52F; 45) which is provided in the insertion section (5) and which is rotatable around the rotation axis, and the adjacent portions (55A to 55F, 56A to 56F; 86A, 86B) which are adjacently provided on both sides of the rotating member (52A to 52F; 45) in the direction along the rotation axis (P1 to P6; C) and to which the rotating member (52A to 52F; 45) is rotatably attached. The cover tube (47) which forms a part of the outer surface of the insertion section (5) is provided in the elastic deformation state so as to apply elastic force toward the inner peripheral side of the insertion section (5). The position of the rotating member (52A to 52F; 45) in the direction along the rotation axis (P1 to P6; C) is adjusted by the elastic force from the cover tube (47), whereby a state where both ends of the rotating member (52A to 52F; 45) in the direction along the rotation axis (P1 to P6; C) are located apart from the adjacent portions (55A to 55F, 56A to 56F; 86A, 86B) is maintained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An insertion instrument comprising:
   an insertion section extending from a proximal side to a distal side along a longitudinal axis;
   a rotating member which is provided in the insertion section, and which is rotatable around a rotation axis that is parallel to the longitudinal axis;
   adjacent portions which are adjacently provided on both sides of the rotating member in a direction along the rotation axis, and to which the rotating member is rotatably attached;
   a cover tube which forms a part of an outer surface of the insertion section, and which is provided in an elastic deformation state so as to apply elastic force toward an inner peripheral side of the insertion section; and
   a protrusion which is provided in the rotating member, and which protrudes toward an outer peripheral side of the insertion section relative to the adjacent portions, the protrusion being configured to press the cover tube from the inner peripheral side of the insertion section and thereby configured to hold the cover tube in the elastic deformation state,
   wherein
   the cover tube which is not in the elastic deformation state includes a distal side tubular portion, a proximal side tubular portion which is located on the proximal side with respect to the distal side tubular portion and which is larger in diameter than the distal side tubular portion, and an intermediate taper portion which extends between the distal side tubular portion and the proximal side tubular portion in a direction along the longitudinal axis and which increases in diameter toward the proximal side,
   in a state where the cover tube is elastically deformed by pressure from the protrusion, the cover tube forms, from a pressure position by a distal end of the protrusion toward the distal side, a distal side dimension changing portion which decreases in dimension in a diametrical direction from the longitudinal axis toward the distal side, and also forms, from a pressure position by a proximal end of the protrusion toward the proximal side, a proximal side dimension changing portion which decreases in dimension in the diametrical direction from the longitudinal axis toward the proximal side, and
   the cover tube is configured to adjust a position of the rotating member in the direction along the rotation axis by the elastic force, and thereby configured to maintain a state where both ends of the rotating member are located apart from the adjacent portions in the direction along the rotation axis.

2. The insertion instrument according to claim 1, wherein
the distal end of the protrusion is configured to press the cover tube at a boundary position between the intermediate taper portion and the proximal side tubular portion, and
the proximal end of the protrusion is configured to press the cover tube by the proximal side tubular portion.

3. The insertion instrument according to claim 2, wherein the cover tube includes an inner peripheral curved surface which is formed in an inner peripheral surface of the cover tube at the boundary position between the intermediate taper portion and the proximal side tubular portion, and which is formed into an arc shape in a section parallel to the longitudinal axis.

4. The insertion instrument according to claim 3, wherein
the protrusion of the rotating member includes a projecting curved surface which forms the distal end of the protrusion, and which is configured to press the cover tube at the inner peripheral curved surface, the projecting curved surface being formed into an arc shape having a first curvature radius in a section parallel to the rotation axis, and
the inner peripheral curved surface of the cover tube is formed into an arc shape having a second curvature radius larger than the first curvature radius in the section parallel to the longitudinal axis.

5. The insertion instrument according to claim 1, wherein
the distal end of the protrusion is configured to press the cover tube in the intermediate taper portion, and
the proximal end of the protrusion is configured to press the cover tube in the proximal side tubular portion.

6. The insertion instrument according to claim 1, wherein the rotating member is a roller which is configured to turn around a turning axis different from the longitudinal axis as the rotation axis.

7. The insertion instrument according to claim 6, wherein the insertion section includes a rotating tubular member which forms the adjacent portions, and to which the roller is turnably attached, the rotating tubular member being configured to rotate around the longitudinal axis together with the roller by the transmission of driving force to the rotating tubular member.

8. The insertion instrument according to claim 7, wherein
the roller includes rollers which are provided apart from one another around the longitudinal axis, and which are configured to rotate together around the longitudinal axis by the transmission of driving force to the rollers,
each of the rollers has a turning axis, and is turnable around the turning axis, and
the cover tube is configured to adjust a position of each of the rollers in a direction along the turning axis by the elastic force.

9. The insertion instrument according to claim 1, wherein
the rotating member is a rotating tubular member which is configured to rotate around the longitudinal axis that is the rotation axis by the transmission of driving force to the rotating tubular member, and
the insertion section includes a base portion which forms the adjacent portions, and to which the rotating tubular member is rotatably attached.

10. An insertion device comprising:
an insertion instrument according to claim 1; and
an assistance tool which is attached to the insertion section in a state to cover the cover tube from an outer peripheral side, and which is rotatable around the longitudinal axis.

11. The insertion device according to claim 10, wherein
the rotating member includes a protrusion which protrudes toward an outer peripheral side of the insertion section relative to the adjacent portions, and which is configured to rotate around the longitudinal axis by the transmission of driving force to the protrusion, and
the assistance tool is configured to be pressed from the protrusion via the cover tube by the rotation of the protrusion around the longitudinal axis, and thereby configured to rotate around the longitudinal axis together with the protrusion.

* * * * *